United States Patent
Ogawa et al.

(10) Patent No.: US 8,436,989 B2
(45) Date of Patent: May 7, 2013

(54) INSPECTION APPARATUS USING A CHIP

(75) Inventors: Yoshimasa Ogawa, Hyogo (JP);
Kazuyuki Kaneda, Hyogo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 279 days.

(21) Appl. No.: 12/923,881

(22) Filed: Oct. 13, 2010

(65) Prior Publication Data
US 2011/0090490 A1    Apr. 21, 2011

(30) Foreign Application Priority Data
Oct. 16, 2009  (JP) .................. 2009-239910

(51) Int. Cl.
*G01N 1/10* (2006.01)
(52) U.S. Cl.
USPC ........................... 356/246; 356/244

(58) Field of Classification Search ........... 356/244–246
See application file for complete search history.

(56) References Cited

U.S. PATENT DOCUMENTS
6,531,095 B2 *  3/2003  Hammer et al. ............... 422/64
2005/0227274 A1  10/2005  Takahashi FOREIGN PATENT DOCUMENTS
JP    2005-300292 A    10/2005
JP    2008-268198 A    11/2008

* cited by examiner

*Primary Examiner* — Tara S Pajoohi Gomez
(74) *Attorney, Agent, or Firm* — Rader, Fishman & Grauer PLLC

(57) ABSTRACT

An inspection apparatus using a chip includes a rotor that holds a chip; a measurement room in which the rotor is provided and a through hole is formed; a light source that emits light for measurement to the chip through the through hole; a light measurement unit that detects the light from the chip, a rotation drive mechanism that rotates the rotor; and a cover member capable of covering or uncovering an opening portion.

4 Claims, 12 Drawing Sheets

Mode 1:
Chip attaching and removing position

Mode 2:
Centrifugation (pre-treatment) position

Mode 3:
Measurement position

INSPECTION APPARATUS USING A CHIP

CROSS-REFERENCES TO RELATED APPLICATION

This application claims priority from Japanese Patent Application Serial No. 2009-239910 filed Oct. 16, 2009, the contents of which are incorporated herein by reference in their entirety.

TECHNICAL FIELD

The present invention relates to an inspection apparatus that uses a chip, and especially relates to an inspection apparatus using a chip, which performs an optical inspection of a sample, using a centrifugal force generated by rotating the chip in which the sample is stored.

BACKGROUND

FIG. 8 is a diagram of a sample component detecting apparatus disclosed in Japanese Patent Application Publication No. 2005-300292. As shown in the figure, a module(s) 201, in which a sample is injected, is held on a disk 202 of the apparatus, and a centrifugal drive mechanism 203 rotates the disk 202, which applies a centrifugal force, and then a light source 204 irradiates, with light, the sample obtained as a result therefrom, so that an optical detection unit 205 detects fluorescence emitted from the sample. Furthermore, Japanese Patent Application Publication No. 2005-300292 discloses that it is possible to offer a sample component detecting apparatus which does not affect a measurement result even in an abnormal condition, such as dust adhering to a microarray.

However, in such an inspection apparatus using a chip disclosed in Japanese Patent Application Publication No. 2005-300292, while the module(s) 201, in which the sample is injected, is held on the disk 202, it is necessary to rotate the disk 202 at a high speed in order to apply a large centrifugal force to the disk 202. Consequently, since impurities, such as dirt and dusts, soar inside the apparatus, there is a possibility that the impurities may adhere to components of an optical component unit 206. When the impurities adhere to the components of the optical component unit 206 and are illuminated with the light from the light source 204 and the light from the sample there is a problem that measurement accuracy is deteriorated.

Detailed description of the problem will be given below. First, (1) when an absorptiometry method is used to detect a sample light from a light source passes through the sample and an optical power detector detects the light intensity. In such a case, the degree of light absorbed in the sample is judged from a light intensity difference between the light intensity of the light source and that of a light detector. However, when impurities adhere to the optical components, the light detector cannot distinguish between the light intensity drop due to absorption of the light intensity in the sample or the light intensity thereof drops since the light is blocked by the impurities, so that a correct measurement result cannot be obtained. Moreover, (2) when a fluorescence measuring method is used to detect a sample, the sample is irradiated with light from a light source, so that the sample is excited to emit fluorescence, so that the fluorescence is detected by the light detector. However, when the impurities adhere to the optical components, the impurities are irradiated with the light, so that the fluorescence is also emitted from the impurities. In this case, the light detector cannot judge whether or not the fluorescence is emitted from the sample or the impurities. Thus, the correct measurement result may not be obtained.

In view of the above-mentioned problems, it is an object of the present invention to offer an inspection apparatus using a chip, in which adhesion of impurities to optical components such as a light measurement unit for detecting a sample is suppressed.

BRIEF DESCRIPTION OF THE DRAWINGS

Other features and advantages of the present inspection apparatus using a chip will be apparent from the ensuing description, taken in conjunction with the accompanying drawings, in which.

DESCRIPTION

Figure 1:
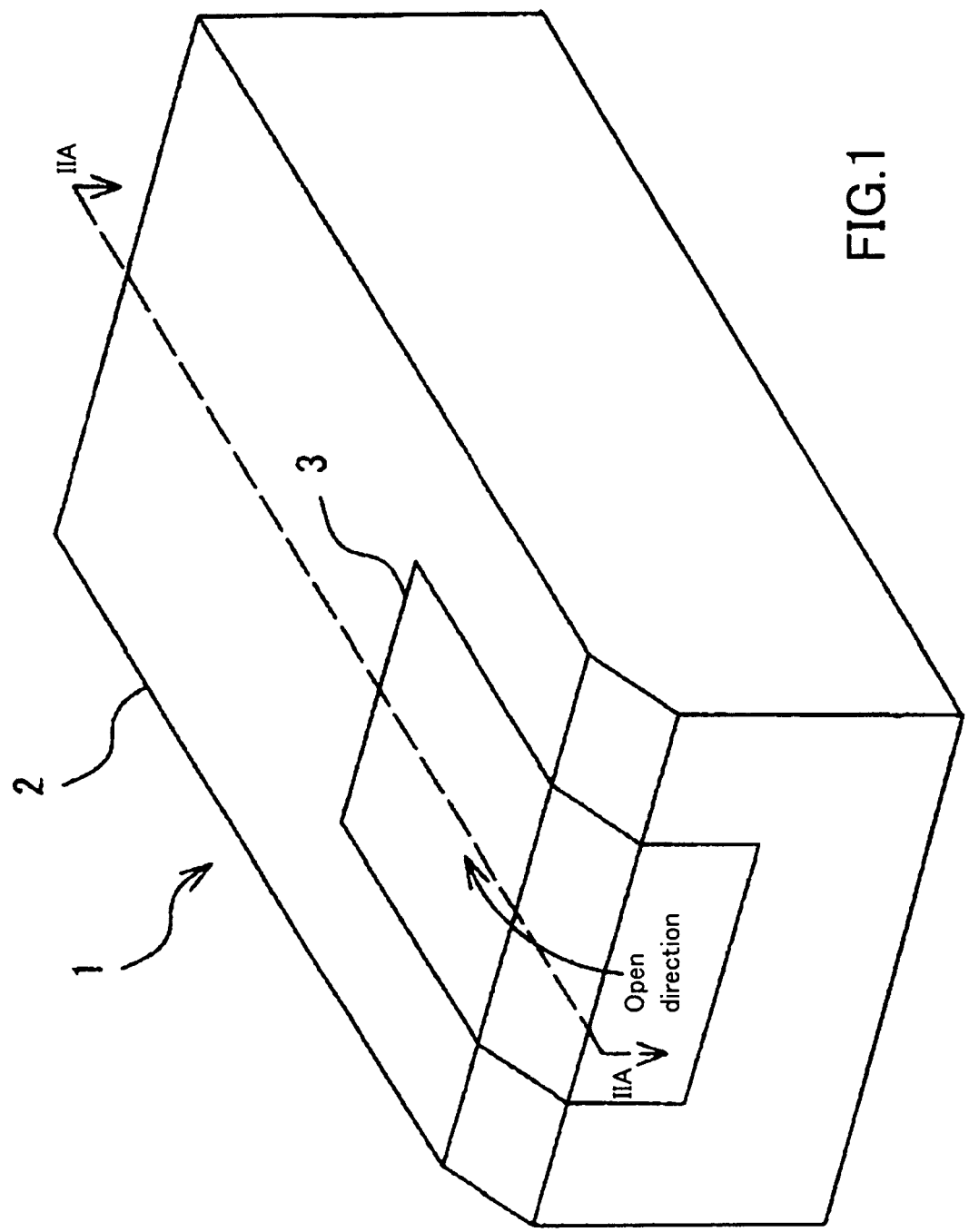
FIG. 1 is a perspective view of an inspection apparatus using a chip according an embodiment of the present invention.

To solve the problem, an inspection apparatus using a chip according to the present invention comprises a rotor that holds a chip; a measurement room in which the rotor is provided and a through hole is formed; a light source unit that emits light for measurement to the chip through the through hole; a light measurement unit which detects the light from the chip, a rotation drive mechanism that rotates the rotor; and a cover member capable of selectively covering or uncovering an opening portion, which is provided between the through hole and an opening of the light measurement unit through which light passes, wherein when the chip is not irradiated with the light and when detection is not carried out by the light measurement unit, the opening portion is covered by the cover member.

The inspection apparatus using a chip may have a hole portion that is formed in the rotor, a projection portion that can be inserted in the hole portion, and a drive mechanism that moves the projection portion and the cover member, wherein while the projection portion is inserted in or removed from the hole portion according to the rotational position of the drive mechanism, the cover member is moved so as to cover or uncover the opening portion.

The inspection apparatus using a chip may have a movable body provided so as to be movable by the drive mechanism, a dog member provided in the movable body, and a position sensor which detects the movement position of the dog member, wherein the rotational position of the drive mechanism is controlled based on a detection result of the position sensor.

Moreover, a control method of the inspection apparatus using a chip may comprise of inserting the projection portion in the hole portion in a state where the opening portion is closed; removing the projection portion from the hole portion in a state where the opening portion is covered and of rotating the rotor; and emitting light and of performing a detection by the light measurement unit in a state where the opening portion is not covered.

In the inspection apparatus using a chip according to the present invention, since the light measurement unit is closed except when the sample is detected by the light measurement unit, the impurities (dirt and dusts) from the measurement room do not enter the light measurement unit.

Therefore, it is possible to prevent the light measurement unit from detecting light emitted from impurities whether reflected irradiated or blocked.

In the inspection apparatus using a chip, the drive mechanism, which moves the cover member, and the drive mechanism, which moves the projection portion, can be configured by a common unit, so that it is possible to miniaturize the apparatus. Moreover, since the rotor is not rotated at time of insertion of the chip, it is possible to easily perform an operation. In the inspection apparatus using a chip, since the position sensor is provided, and the movement position of the drive mechanism is controlled based on a detection result of the position sensor, an operation of the projection portion and the cover member can be correctly controlled.

In the inspection apparatus using a chip, it is possible to organically, sequentially and certainly control covering and uncovering of the opening portion according to timing of light measurement or non-light measurement by the light measurement unit, and to control non-rotation and rotation of the rotor according to a state where the projection portion is inserted or not.

Description of the features of the present invention will be given below. Adhesion of impurities such as dirt and dusts, to a light measurement unit for detecting a sample with light is suppressed. In a single drive mechanism, rotation regulation of a rotor is controlled by a projection portion interlocked with a driving shaft of the drive mechanism. Opening-and-closing of a cover member is controlled through a movable body driven by the drive mechanism. Further, movement of an object to be opened and closed is controlled, i.e. opening and closing of a lid portion is controlled through the movable body driven by the drive mechanism.

Figures 2A, 2B:
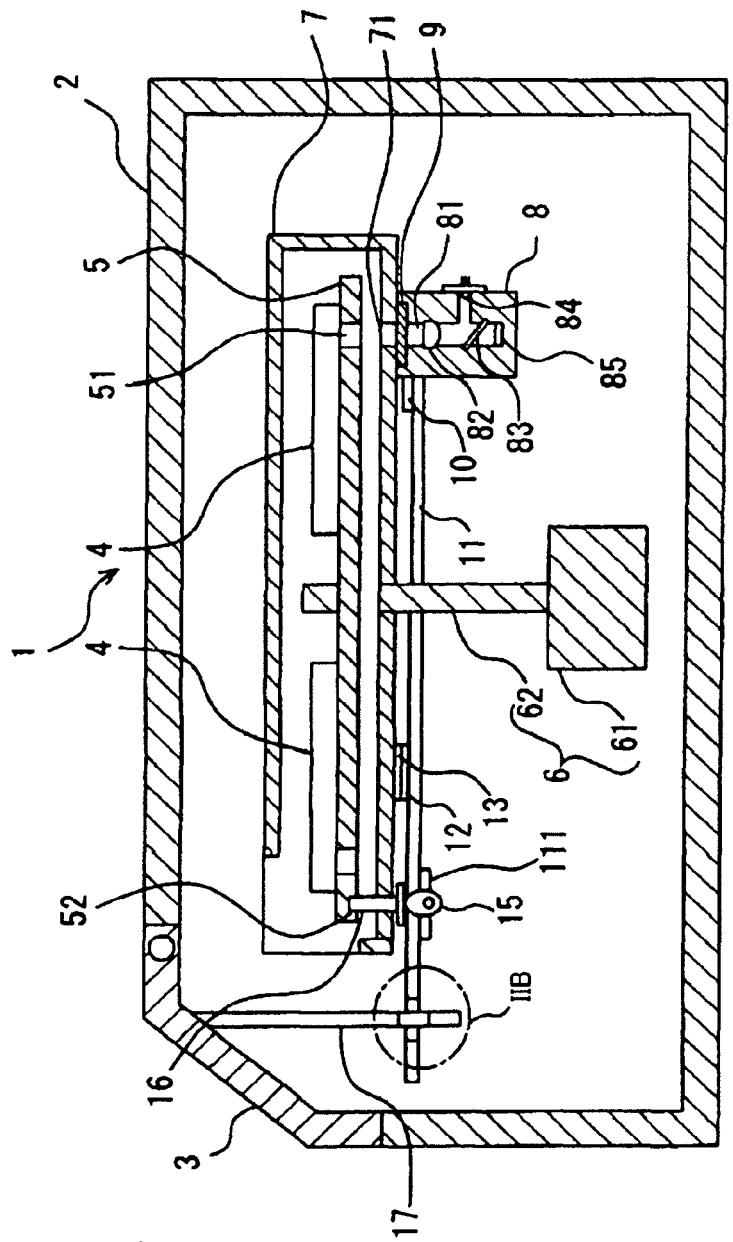
FIG. 2A is a cross sectional view of an inspection apparatus using a chip, taken along a line IIA-IIA of FIG. 1.
FIG. 2B is an enlarged perspective view of a portion IIB which regulates opening and closing of a lid shown in the cross sectional view taken along a line IIA-IIA of FIG. 1.
Figure 3:
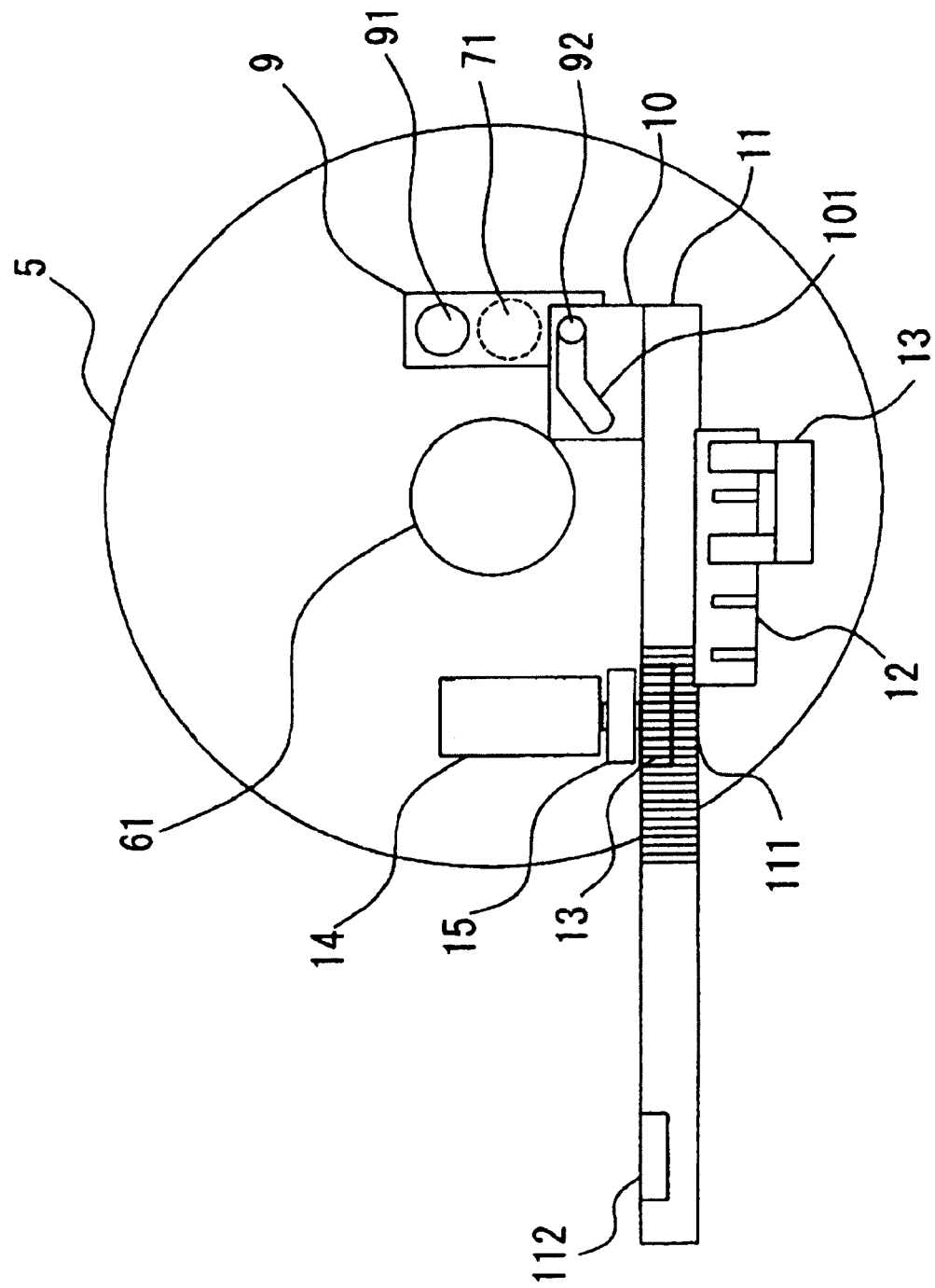
FIG. 3 is a bottom view of a light measurement unit using a chip, which is viewed in a direction from a lower part toward an upper part of FIG. 2A, wherein the measurement unit, an outer cover, and the lid are omitted.

Description of an embodiment of the present invention will be given below referring to FIGS. 1-7. FIG. 1 is a perspective view of an appearance of an inspection apparatus using a chip according the embodiment of the present invention. As shown in FIG. 1, a lid 3, which can be opened and closed, is provided in part of an outer cover 2 of the inspection apparatus 1 using a chip, to enable access to the inside of the apparatus 1. When the lid 3 is opened, the chip to be installed in a rotor, which is provided inside the apparatus 1, can be attached or removed. FIG. 2A is a cross sectional view of the inspection apparatus using a chip, taken along a line IIA-IIA of FIG. 1, and FIG. 2B is an enlarged perspective view of a portion IIB regulates opening and closing of the lid of FIG. 2A. FIG. 3 is a bottom view of a light measurement unit using a chip when viewed in a direction from a lower part toward an upper part of a measurement room of FIG. 2A, wherein the light measurement unit, the outer cover and the lid are omitted. As shown in FIG. 2A, the rotor 5, which holds the chip 4; a rotation drive mechanism 6 that drives and rotates the rotor 5; the measurement room 7 that surrounds the rotor 5; and the light measurement unit 8 that irradiates a sample in the chip 4 with light and that detects light, such as fluorescence emitted from the sample, are provided inside the outer cover 2. The rotation drive mechanism 6 has a drive mechanism 61 and a rotational axis 62. The rotor 5 is approximately disk-shaped, and the rotational axis 62 is connected to the rotor 5 at the center position of the rotor 5. A through hole 51, which leads to the chip 4 held therein ("to lead" means "to be connected as an optical path", as described below), is provided in the rotor 5. A through hole 71, which leads to the through hole 51 formed in the rotor 5, is provided in the measurement room 7. The light measurement unit 8 is arranged outside the measurement room 7 and in an outward direction of the through hole 71 of the measurement room 7. A cover member 9, which can cover and uncover an opening portion 81 of the light measurement unit 8, is provided between the through hole 71 and the opening portion 81, through which light to be detected is emitted and enters. When light is not emitted from the light measurement unit 8 or when light is not detected by the light measurement unit 8, the opening portion 81 is covered by the cover member 9.

The light measurement unit 8 has a lens 82 that is arranged along an optical axis with reference to the through hole 71 of the measurement room 7, a half mirror 83, which is arranged along the optical axis of the lens 82, a light source 84, which is arranged at a position where the light source 84 optically faces the lens 82 through the half mirror 83, and a light detection unit 85 that is provided in a back side of the half mirror 83 and that optically faces the lens 82 through the half mirror 83. A condensing lens, which condenses light, is used as the lens 82, for example, a planoconvex lens. As the light source 84, for example, a light emitting diode (LED) is used. As the light detection unit 85, for example, a photomultiplier (Photo-Multiplier Tube: PMT) or a photo diode is used.

As shown in FIG. 3, a through hole 91 and a pin 92 are provided on the cover member 9. The movable member 10 having a groove 101, with which the pin 92 is slidably brought in contact, is provided in an outward direction of the cover member 9. The movable member 10 is connected to the movable body 11. Moreover, as shown in FIG. 2A, the movable body 11 is located in a lower part of the measurement room 7, and extends in an outward direction toward the lid 3 from around the light measurement unit 8.

Moreover, as shown in FIG. 3, a dog member 12 is provided in the movable body 11. The dog member 12 is detected by a position sensor 13. Furthermore, a (rack) gear 111 is provided in the movable body 11, and a (pinion) gear 13, which is engaged, with the (rack) gear 111 is provided. The (pinion) gear 13 is connected with a drive mechanism 14 to be driven and rotated by the drive mechanism 14. The drive mechanism 14 is provided on an outer face of the measurement room 7 and a cam 15 is connected to the drive mechanism 14.

As shown in FIG. 2A, a projection portion 16 is provided on (in contact with) the cam 15, wherein when the cam 15 is rotated by rotary drive of the drive mechanism 14 the projection portion 16 is moved up-and-down directions in the figure by the rotation of the cam 15. With the movement of the projection portion 16 in the up and down directions of the figure, an end portion of the projection portion 16 can be inserted in a hole portion 52 formed in the rotor 5.

As shown in FIG. 2B, a cutout portion 112 is formed in an end portion of the movable body 11 in a lid 3 side, and an opening-and-closing regulation member 17 extends from an inner face of the lid 3 is arranged in the cutout portion 112. Further, a cutout portion 171 is formed in the opening-and-closing regulation member 17.

A function of the drive mechanism 14, which drives the movable body 11, is summarized below. The hole portion 52 is formed in the rotor 5, and the projection portion 16, which is inserted and arranged in a through hole formed in the measurement room 7, is provided so that the projection portion 16 may be inserted in the hole portion 52. Further, while the movable body 11, which moves the cover member 9, is driven, the drive mechanism 14, to which a motion conversion member (cam) 15 for converting rotational movement into a linear motion is connected, is provided on the measurement room 7. A control unit 18 (FIG. 4), which controls the rotation drive mechanism 6 and the light source unit 8, has functions for driving the drive mechanism 14 so that the motion conversion member (cam) 15 moves the projection portion 16, and for moving the cover member 9 to cover or uncover an opening 81.

As disclosed in Japanese Patent Application Publication No. 2008-268198, a sample such as blood is enclosed in the chip 4.

Figure 4:
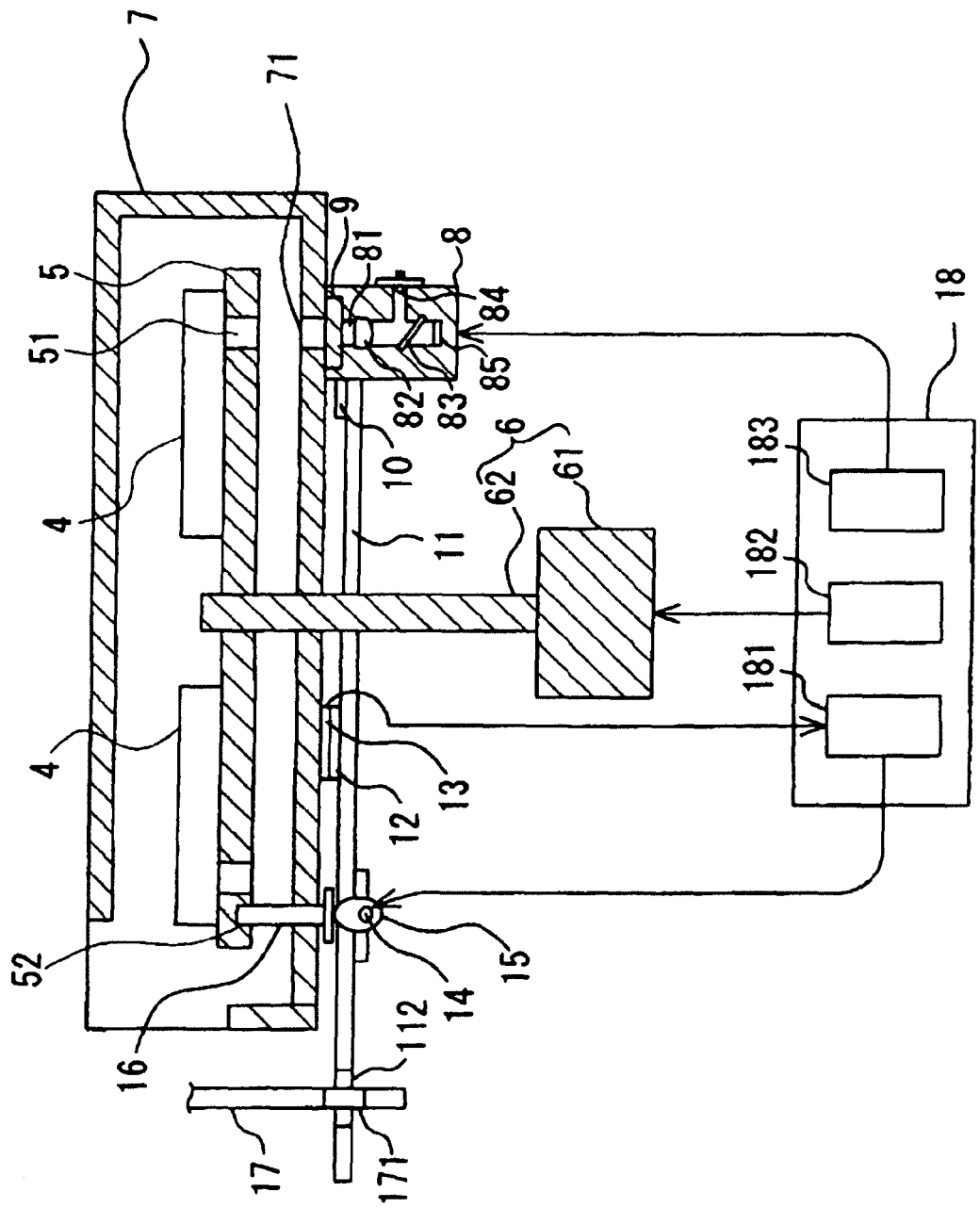
FIG. 4 is a schematic block diagram of the system configuration of an inspection apparatus using a chip according to an embodiment.

FIG. 4 is a schematic block diagram of a system configuration of the apparatus 1. As shown in the figure, the control unit 18 is equipped with a position control unit 181, a rotation drive mechanism control unit 182, and a light measurement control unit 183. The position control unit 181 detects the position of the dog member 12 by the position sensor 13, and controls driving of the drive mechanism 14 according to a drive command signal given from the control unit 18, to rotate the cam 15 and/or to move the movable body 11. According to the drive command signal given from the control unit 18, the rotation drive mechanism control unit 182 controls the rotation drive mechanism 6, rotates the rotor 5, and positions it in a predetermined rotation position. The light measurement control unit 183 inputs, into a light source 84, a lighting command signal given from the control unit 18, and receives a detection result in a light detection unit 85. In addition, the other elements of FIG. 4 that are respectively indicated by the same numerical references as those shown in FIG. 2A correspond to the same elements of FIG. 2A.

Figure 5A:
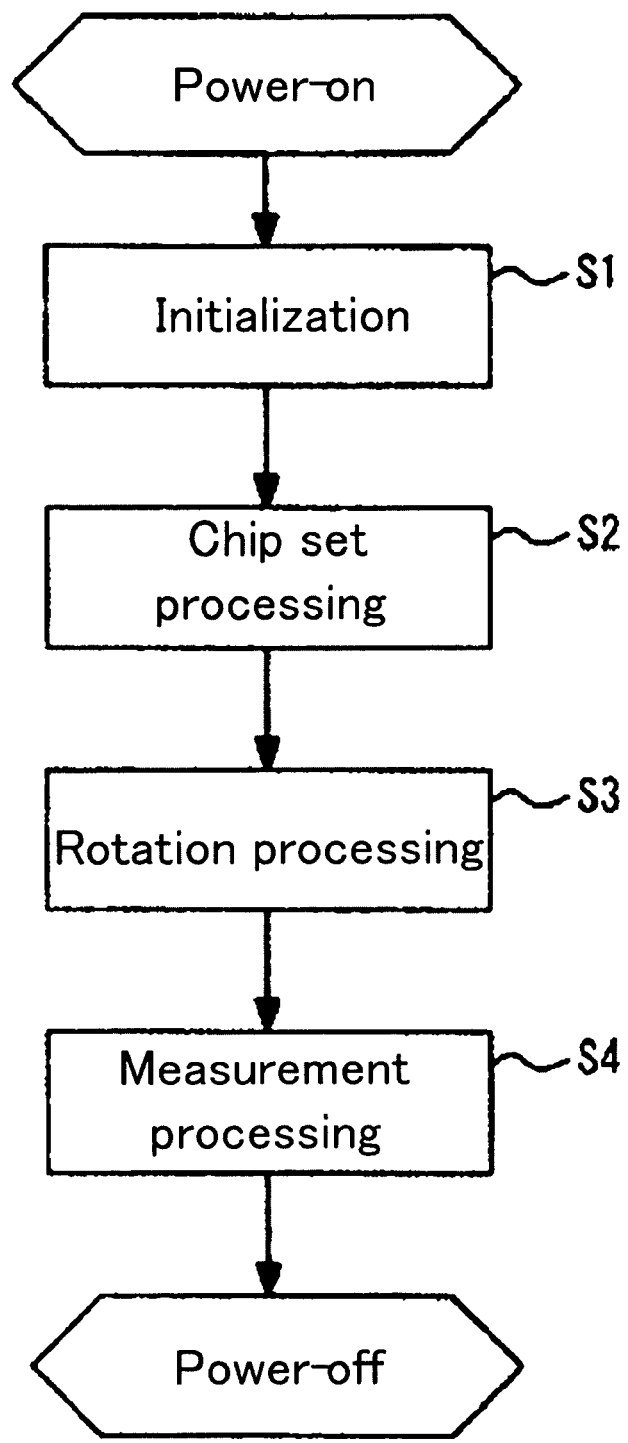
FIGS. 5A to 5D are flow charts showing a processing procedure of an inspection apparatus using a chip according to an embodiment.

Next, a procedure of the inspection apparatus 1 using a chip will be described, referring to FIGS. 4-7. FIG. 5A is a flow chart, which generally shows an entire process for measuring a sample held in the chip 4 of the inspection apparatus 1. First, in Step S1, an initialization processing of the inspection apparatus 1 using a chip is performed. In this process, the processing is performed so that the chip 4 can be inserted. Next, in Step S2, the chip 4 is set to the rotor 5 and then a rotation processing is performed in Step S3. The rotation processing includes weighing of the sample, mixing of the sample and a test reagent, and transporting the liquid to the measurement area in the chip 4. In Step S4, a measurement processing is performed to the sample, which is processed in the measurement area, and then a power supply is turned off after the measurement processing is completed.

Next, detail description of each processing (the initialization processing, the chip set processing, the rotation processing process, the measurement processing process) will be given below.

Figure 5B:
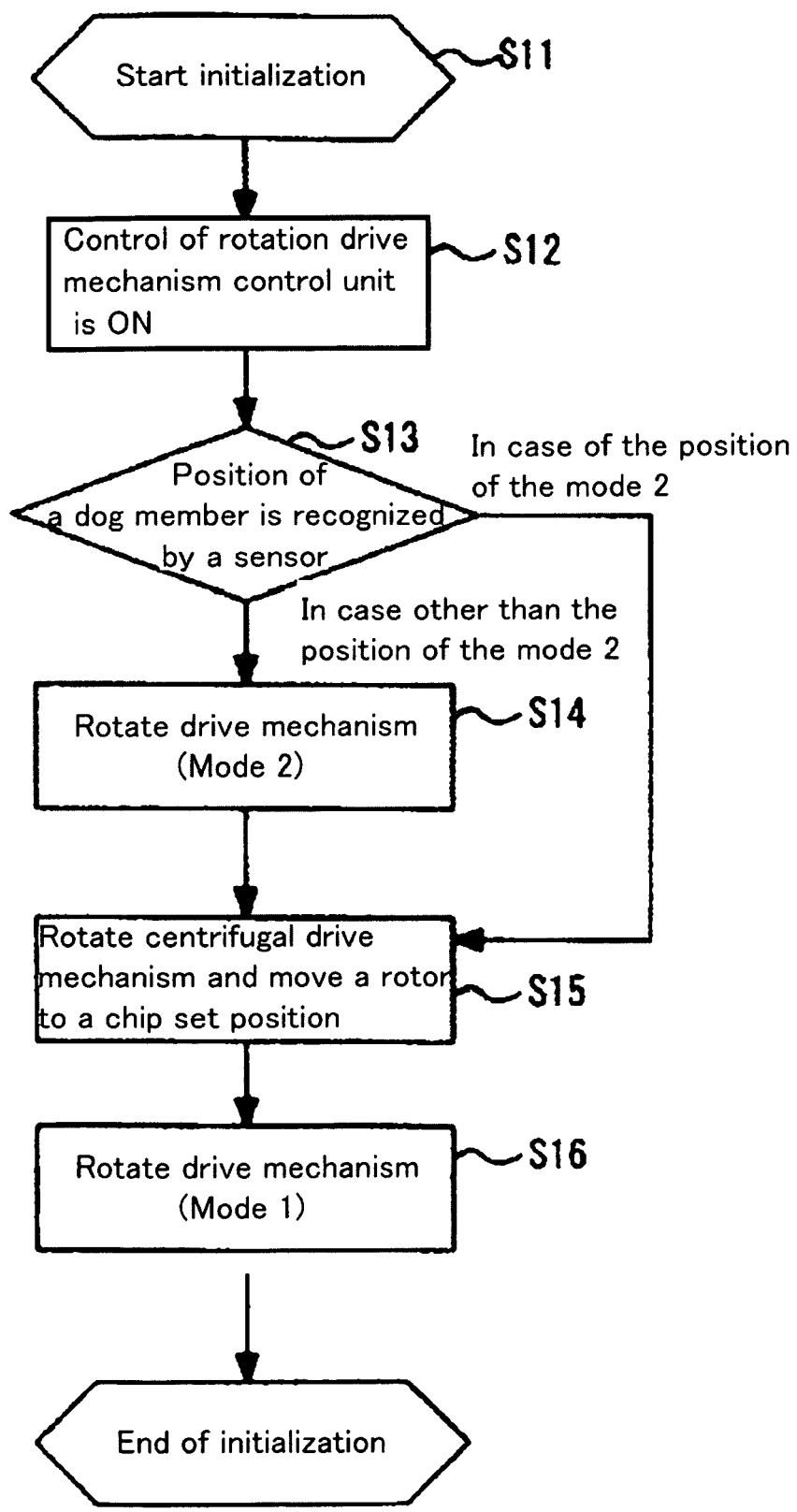

FIG. 5B is a detailed flow chart of the initialization processing (Step S1) performed before setting the chip 4 shown in FIG. 5A. As for the initialization processing, initialization of the apparatus is started when the power supply is turned on. First, in Step S11, the power supply (not shown) is turned on based on a power supply command so that electric power supply to the control unit 18 shown in FIG. 4 is started. The control unit 18, to which the electric power is supplied, turns on the rotation drive mechanism control unit 182 in Step S12. Next, in Step S13, the control unit 18 inputs a reading power supply command into the position sensor 13 from the position control unit 181, and recognizes the position of the movable body 11 according to the existence/nonexistence of the cutout portions of the dog member 12, which is read by the position sensor 13.

Figure 6:
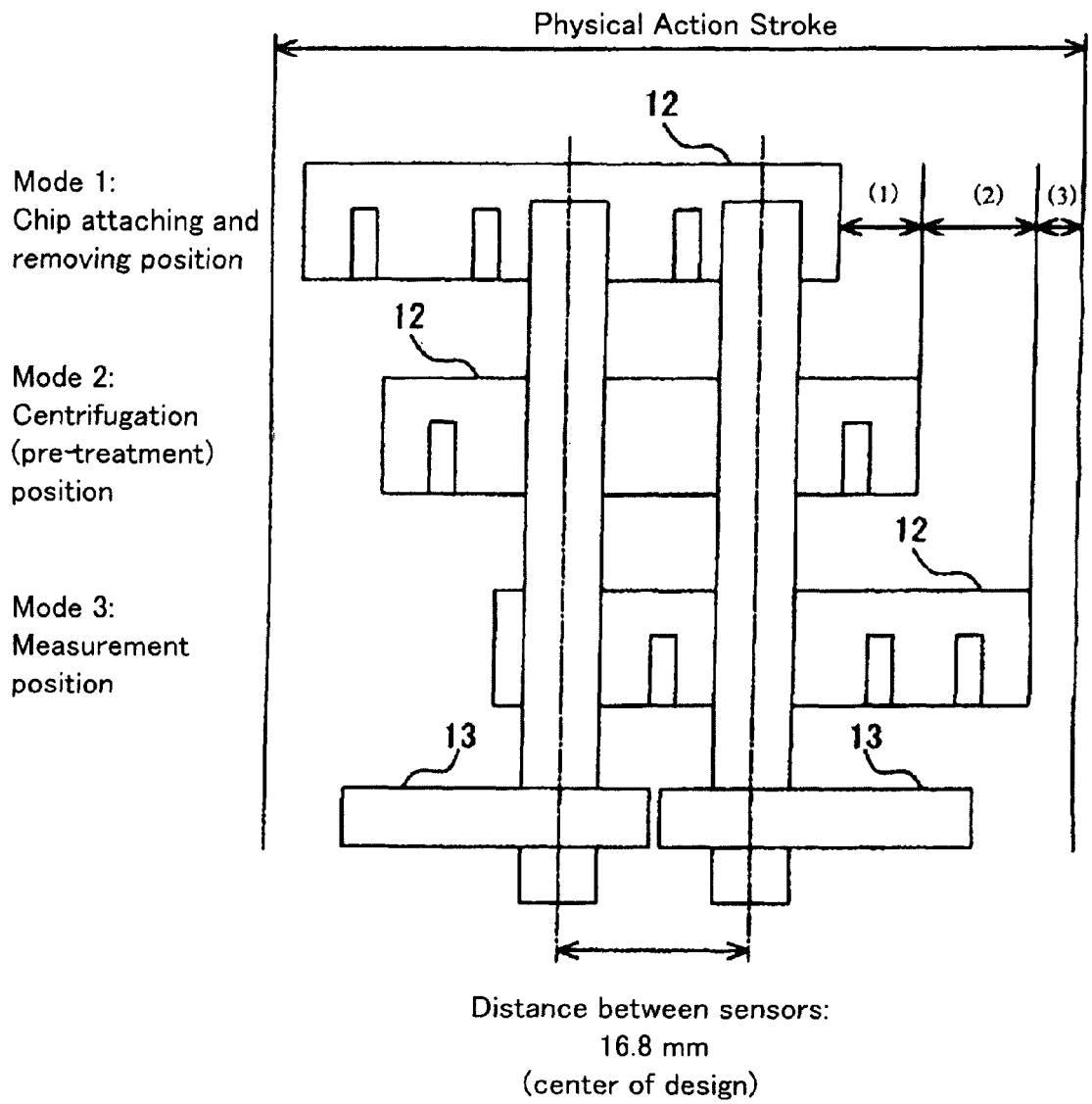
FIG. 6 is a diagram showing an example of the physical relationship of a position sensor and a dog member in each of modes 1-3.

Here, detailed description of the position recognition of the movable body 11 will be given below, referring to FIG. 6. Two or more cutout portions are formed in the dog member 12 (in FIG. 6, four cutout portions are formed). On the other hand, two sensors are provided as the position sensor 13, and these two sensors detect the existence/nonexistence of the cutout portions of the dog member 12. When the cutout portion is located at one of the two sensors, which is in the right hand side of the figure, and no cutout portion is located at the other sensor which is in the left hand side of the figure, it is possible to recognize that the movable body 11 is located at the position of the mode 1. Thus, when those two sensors are used, it is possible to detect three positions of the dog member 12 (the modes 1-3). In addition, a concrete example of the physical relationship of the position sensors 13 and the dog member 12 in each of the modes 1-3 is described below. When a distance between the two position sensors 13 is 16.8 mm, a pitch diameter of the (pinion) gear used is φ10 mm, a stop angle between the mode 1 and the mode 2 (the mode 1->modes 2) is 90 degrees, and a stop angle between the mode 2 and the mode 3 (the mode 2->modes 3) is 135 degrees. A movement distance (1) from the mode 1 to the mode 2 is 10×3.14×90/360=7.85 mm, a movement distance (2) from the mode 2 to the mode 3 is 10×3.14×135/360=11.80 mm, and a margin (3), by which the mechanism stops, is 1 mm.

Figure 7A:
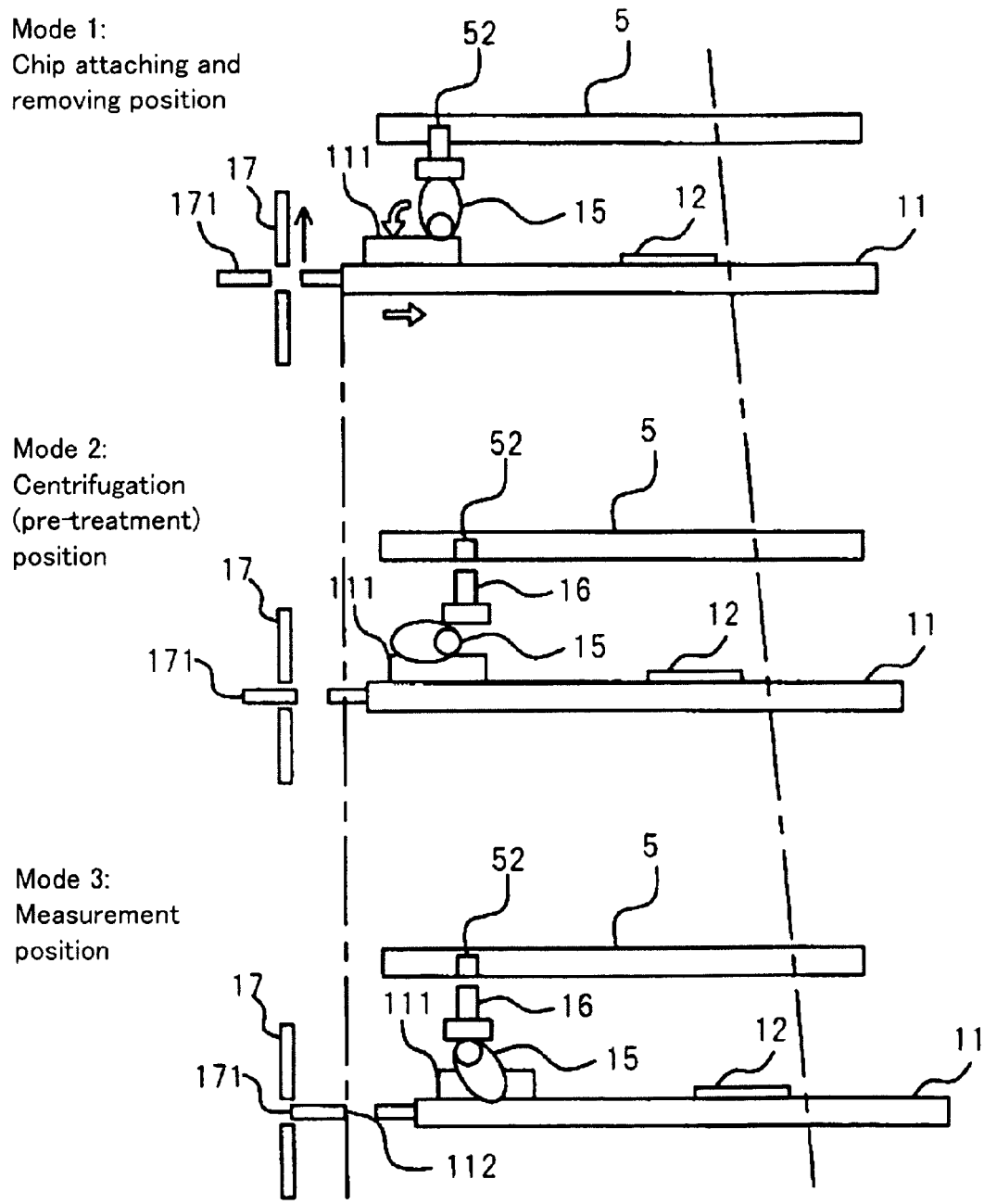
FIGS. 7A and 7B are diagrams showing a displacement of a movable body 11, a cover member 9, a projection portion 16, and an cutout portion 112 of the movable body 11 in each position in a mode 1 (chip removable position), a mode 2 (centrifugal pretreatment position), and a mode 3 (measurement position)
Figure 7B:
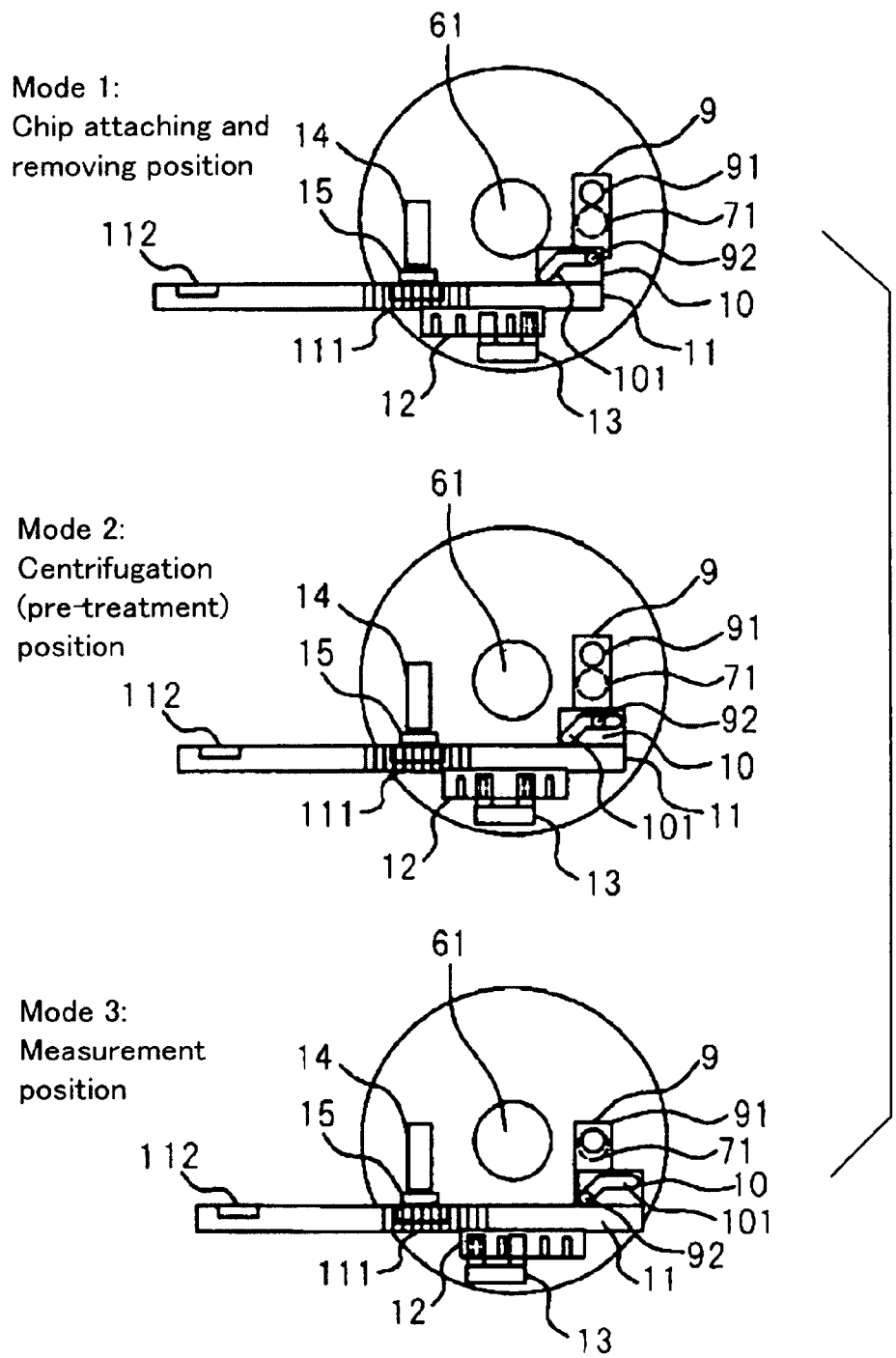
Figure 8:
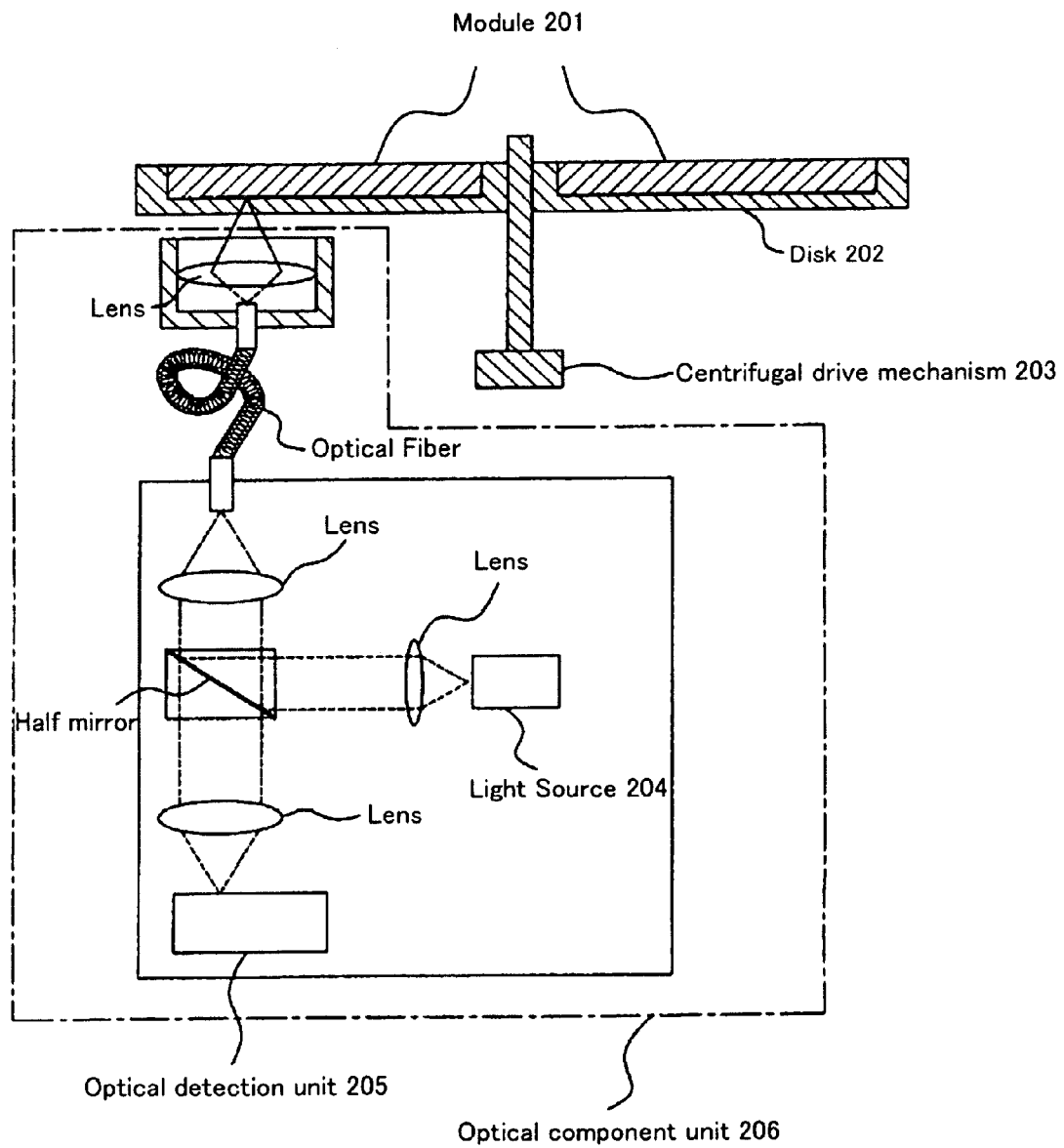
FIG. 8 is a diagram showing a schematic structure of a conventional inspection apparatus using a chip.

Furthermore, description of a state of the movable body 11 in each mode of the inspection apparatus 1 using a chip will be given below referring to FIGS. 7A and 7B. The mode 1 means, as shown in FIG. 2A, a state where the lid 3 can be opened and closed (a state where the cutout portion 171 of the opening-and-closing regulation member 17 extending from the inner face of the lid 3, and the cutout portion 112 of the movable body 11 are in the same position as each other, as shown in FIG. 2B); where the rotor 5 cannot be rotated (the projection portion 16 connected to the cam 15 is inserted in the hole portion 52 of the rotor 5, whereby since the cam 15 is connected to the drive mechanism 14 and the drive mechanism 14 is connected to the measurement room 7, rotation of the rotor 5 is regulated by the projection portion 16); and where an optical path is closed (a state where the cover member 9 is arranged between the opening portion 81 of the light measurement unit 8 and the through hole 71 of the measurement room 7, so that the optical path which leads to the chip 4 is blocked by the cover member 4, that is, a state where the opening portion 81 of the light measurement unit 8 is closed). The mode 2 means a state where the lid 3 cannot be opened and closed (a state where a portion other than the cutout portion 112 of the movable body 11 is located at the position of the cutout 171 of the opening-and-closing regulation member 17 extending from the inner face of the lid 3, so that the lid 3 cannot be opened even when the lid 3 is tried to be opened, since it is caught in the movable body 11); where the rotor 5 can be rotated (a state where the projection portion 16 is not inserted in the hole portion 52 of the rotor 5), and where the opening portion 81 of the light measurement unit 8 is closed as in the mode 1. The mode 3 means a state where the lid 3 cannot be opened and closed, as in the mode 2; where the rotor 5 can be rotated as in the mode 2, and where the opening portion 81 of the light measurement unit 8 is not closed (a state where the through hole 91 provided in the cover member 9 is connected to the through hole 71 of the measurement room 7, so that the optical path, which leads from the light measurement unit 8 to the chip 4, is formed).

Next, the process returns to Step S13 of FIG. 5B, in which the position of the movable body 11 is recognized, so that whether it is in the state in the mode 2, is checked. When it is not in the mode 2, in Step S14, a drive signal is outputted from the position control unit 181, so that the drive mechanism 14 is rotated, which changes the state to the mode 2. In the case of the mode 2, the process proceeds to Step S15. In Step S15, the control unit 18 transmits a drive command signal to the rotation drive mechanism control unit 181, so that the centrifugal drive mechanism 61 of the rotation drive mechanism 6 is rotated by the rotation drive mechanism control unit 181, where the rotor 5 is moved to the position where the chip is set. At this time, as shown in FIGS. 7A and 7B, in the mode 2, the rotor 5 can be rotated. Even when the rotor 5 is rotated, since the optical path of the light measurement unit 8 is closed by the cover member 9 that is in contact with an outer face of the opening portion 81 of the light measurement unit 8, it is possible to suppress entry of impurities (dirt and dusts, etc.) produced inside the measurement room 7 to the inside of the light measurement unit 8 due to the rotation of a rotor 5.

When the rotor 5 moves to the chip set position in Step S16, the control unit 18 rotates the drive mechanism 14 by the position control unit 181 until the dog member 12 is moved to the position in the mode 1 from the position in the mode 2. At this time, in this apparatus 1, when the drive mechanism 14 is rotated from the position in the mode 2 to the position in the mode 1, the (pinion) gear 13 connected to the end portion of the drive mechanism 14 and the (rack) gear 111 of the movable body 11 are engaged with each other and rotated, so that the movable body 11 moves to the left hand side of FIG. 7A. Consequently, the cutout portion 171 of the opening-and-closing regulation object 17 and the cutout portion 112 of the movable body 11 come to the same position and the lid 3 can be opened and closed. At the same time, the cam 15 connected to the drive mechanism 14 is rotated; the projection portion 16 connected to the cam 15 moves to an upper part of the figure, so that the projection portion 16 and the hole 52 of the rotor 5 go into a fitting state; and the rotation of the rotor 5 is regulated. Moreover, as shown in FIG. 7B, since the movable member 10 is connected to the end portion (an end portion that is different from that in the side of the cutout portion 112) of the movable body 11, the movable member 10 is moved with the movement of the movable body 11. However, since the groove 101 formed on the movable member 10 extends along the movement direction of the movable body 11 and the pin 92 of the cover member 9 arranged on the groove 101 merely slides on and along the groove 101 of the movable member 10, the cover member 9 having the pin 92 does not move and the opening 81 of the light measuring unit 8 remains closed.

Next, the chip set processing (Step S2) shown in FIG. 5A will be described below in detail. As shown in FIG. 2A, in the chip set processing, since the rotor 5 of the inspection apparatus 1 using a chip is located in the position where the chip 4 can be set, and it is in the mode 1, the lid 3 can be opened, and since the rotor 5 does not rotate when the chip 4 is set to the rotor 5, the chip may be set successfully. Moreover, although there is a possibility that the impurities (dirt and dusts) from the outside of the lid 3 may enter the inside of the measurement room 7 when the lid 3 is opened, since the opening 81 of the light measuring unit 8 is closed by the cover member 9, it is possible to prevent such impurities (dirt and dusts) from entering the light measuring unit 8. In this chip set processing, when another chip 4 is set after one chip 4 is set, the process of Steps S14 to S16 are repeated to set a additional chip 4 after closing the lid 3. Thus, these steps are repeated according to the number of chips 4 to be set.

Figure 5C:
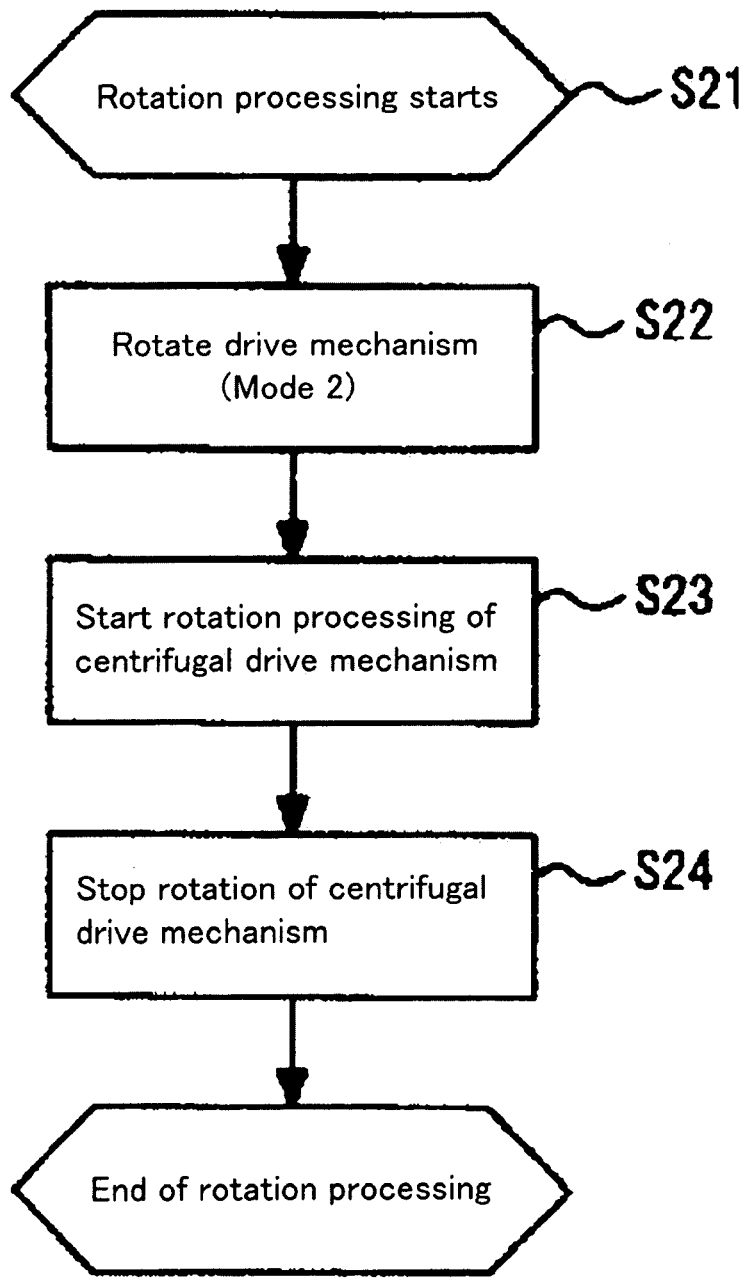

FIG. 5C is a flow chart showing a detailed rotation processing process (Step S3) shown in FIG. 5A. In the rotation processing process, rotation processing starts after the chip 4, required for the rotor 5, is set in Step S21. Next, in Step S22, in a state where the lid 3 of the apparatus 1 is closed, the control unit 18 rotates the drive mechanism 14 until the dog member 12 moves to the position in the mode 2 from the position in the mode 1 by the position control unit 181. At this time, when the drive mechanism 14 is rotated from the position in the mode 1 to the position in the mode 2 in the apparatus 1, the (pinion) gear 13 connected to the end portion of the drive mechanism 14 and the (rack) gear 111 of the movable body 11 are engaged and rotated, so that the movable body 11 moves to the right hand side of FIG. 7A and the movable body 11 is caught by the cutout portion 171 of the opening-and-closing regulation object 17, whereby the lid 3 cannot be opened and closed. At the same time, the cam 15, which is connected to the drive mechanism 14, is rotated; the projection portion 16, which is connected to the cam 15, moves to a lower part of the figure, so that the fitting state of this projection portion 16 and the hole 52 of the rotor 5 is canceled; and, thus, the rotor 5 can be rotated. Moreover, as shown in FIG. 7B, although the movable member 10 is moved with the movement of the movable body 11 in a side of the end portion (an end portion which is different from that in the side of the cutout portion 112) of the movable body 11, since the groove 101 formed on the movable member 10 extends along the movement direction of the movable body 11 and the pin 92 of the cover member 9 arranged on the groove 101 merely slides on and along the groove 101 of the movable member 10, the cover member 9 does not move.

Next, in Step S23, the control unit 18 rotates the centrifugal drive mechanism 61 by the rotation drive mechanism control unit 181. At this time, to apply a centrifugal force required for processing of separation, stirring, etc. to a sample held by the chip 4, the rotation drive mechanism control unit 182 changes the rotational speed of the centrifugal drive mechanism 61. Although impurities (dirt and dusts) soar inside the measurement room 7 due to the rotation of the centrifugal drive mechanism 61, since the opening 81 of the light measurement unit 8 is closed by the cover member 9 it is possible to prevent the impurities from adhering to optical components of the measurement unit 8. In Step S24, the control unit 18 stops the rotation of the centrifugal drive mechanism 61 when a predetermined rotation drive by the rotation drive mechanism control unit 182 is completed, which ends the rotation processing.

Figure 5D:
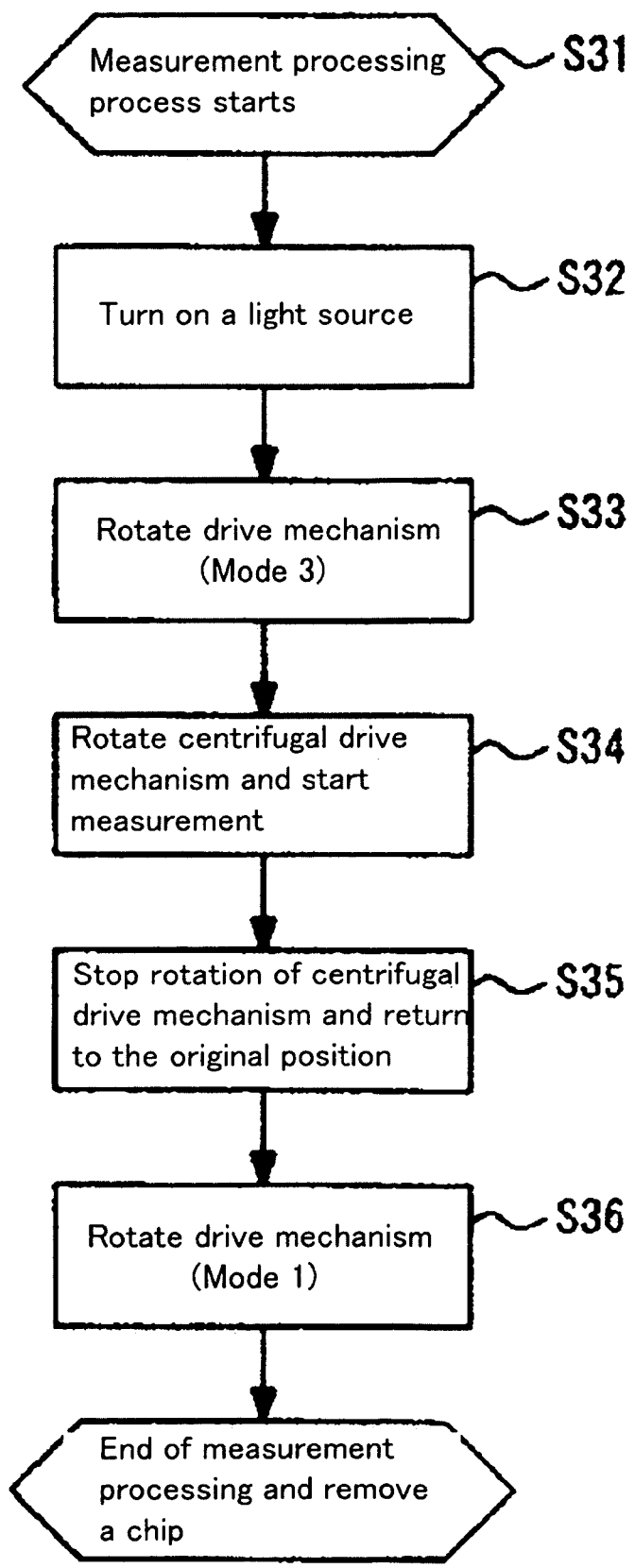

FIG. 5D is a flow chart showing a detailed measurement processing process (Step S4) shown in FIG. 5A. In Step S31, the measurement processing process starts when processing of the sample is completed and the sample is located in the measurement area (not shown) of the chip 4. In Step S32, the control unit 18 turns on the light source 84 by the light measurement control unit 182, whereby light from the light source 84 is reflected by a half mirror 83, so as to enter a lens 82.

Next, in Step S33, the control unit 18 rotates the drive mechanism 14 by the position control unit 181 until the dog member 12 moves to the position in the mode 3 from the position in the mode 2. At this time, when the drive mechanism 14 is rotated from the position in the mode 2 to the position in the mode 3 in the apparatus 1, the (pinion) gear 13 connected to the end portion of the drive mechanism 14 and the (rack) gear 111 of the movable body 11 are engaged and rotated so that the movable body 11 moves to the right hand side of FIG. 7A. Thus, the movable body 11 continues to be caught by the cutout portion 171 of the opening-and-closing regulation object 17, so that the lid 3 cannot be opened and closed. At the same time, the cam 15 that is connected to the drive mechanism 14 is rotated; the projection portion 16 that is connected to the cam 15 remains at a lower part of the figure, so that the fitting state of this projection portion 16 and the hole 52 of the rotor 5 remains canceled; and, thus, the rotor 5 can be rotated. Moreover, as shown in FIG. 7B, the movable member 10 is moved with the movement of the movable body 11 in a side of the end portion (an end portion which is different from that in the side of the cutout portion 112) of the movable body 11. The groove 101 formed on the movable member 10 has a portion extending along the direction in which the movable body 11 moves, and a portion extending along a direction inclines with respect to the direction in which the movable body 11 moves. The cover member 9 is moved as the pin 92 of the cover member 9 slides on the groove 101, which is formed in the inclining direction, and the hole 91 formed on the cover member 9 and the through hole 71 of the measurement room 7 are connected, so that the opening 81 of the light measuring unit 8 is uncovered, whereby the optical path is formed to lead to the chip 4.

Next, in Step S34, in the state where the optical path of the light measuring unit 8 is formed to lead to a chip 4, the control unit 18 rotates the centrifugal drive mechanism 61 by the rotation drive mechanism control unit 182, which starts measurement at the light measuring unit 18. At this time, since the sample is measured in the inside of the chip 4, the rotation drive mechanism control unit 182 drives and rotates the centrifugal drive mechanism 6 at a rotational speed lower than a rotational speed at which the sample is processed. Where the centrifugal rotation of the rotor 5 is carried out, light from the light source 84 is condensed by the lens 82, passes through the through hole 71 of the measurement room 7 and the through hole 51 of the rotor 5 from the opening 81, and emitted onto the measurement area of the chip 4. The sample located in the measurement area of the chip 4 emits fluorescence when the sample is irradiated with light. This fluorescence passes through the through hole 51 of the rotor 5, the through hole 71 of the measurement room 7, through the opening 81, and enters the lens 82 where it will be. The light condensed by the lens 82 passes through the half mirror 83 and enters the light detection unit 85 for detection.

Next, in Step S35, after the measurement in the chip 4 is completed, the control unit 18 stops the rotation of the centrifugal drive mechanism 6 by the rotation drive mechanism control unit 182 at the origin point to return it to the original point. Here, the "origin point" corresponds to the position of the rotor 5 where the chip 4 is taken out.

Next, in Step S36, the control unit 18 rotates the drive mechanism 14 by the position control unit 181 until the dog member 12 moves to the position in the mode 1 from the position in the mode 3. At this time, when the drive mechanism 14 is rotated from the position in the mode 3 to the position in the mode 1 in the inspection apparatus 1 using a chip, the (pinion) gear 13 connected to the end portion of the drive mechanism 14 and the rack gear 111 of the movable body 11 are engaged and rotated, so that the movable body 11 moves to the left hand side of FIG. 7A, whereby the cutout portion 171 of the opening-and-closing regulation object 17 and the cutout portion 112 of the movable body 11 come to the same position allowing the lid 3 to be opened and closed. At the same time, the cam 15 that is connected to the drive mechanism 14 is rotated, so that the projection portion 16 connected to the cam 15 moves to an upper part of the figure, whereby the projection portion 16 and the hole 52 of the rotor 5 go into a fitting state where the rotation of the rotor 5 is regulated. Moreover, as shown in FIG. 7B, although the movable member 10 is moved with the movement of the movable body 11 in a side of the end portion (an end portion which is different from that in the side of the cutout portion 112) of the movable body 11, and when the pin 92 of the cover member 9 slides along the direction in which the movable body 11 moves after the pin 92 of the cover member 9 slides on the groove 101 of the movable member 10 that is directed in the inclined direction, the cover member 9 slides on the outer face of the light measurement unit 8, so that the opening portion 81 of the light measurement unit 8 is closed by the cover member 9. At this time, since the inspection apparatus using a chip according to the present invention can suppress adhesion of impurities except when the optical components that form the light measurement unit 8 measures the sample, it is possible to suppress an error of measurement due to the impurities to obtain an accurate measurement. The measurement processing ends after shifting to the mode 1. After the measurement processing completes, the lid 3 can be opened, and since the rotor 5 is not rotated the chip 4 can be removed suitably. Since the opening portion 81 of the light measurement unit 8 is in the closed state at this time, even if an operation for removing the chip 4 is performed, it is possible to prevent the impurities, which enters from the outside, from adhering to the optical components of the light measurement unit 8. In addition, although the case where the light measurement unit 8 detects fluorescence is described in the above embodiments, such detection may be performed by the light measurement unit 8 using an absorption photometry. In such a case, it is possible to solve the problem (1) described above (when impurities adhere to the optical components, the light detector cannot distinguish between whether the light intensity thereof drops due to absorption of the light intensity in the sample and whether the light intensity drops since the light is blocked by the impurities, so that a correct measurement result cannot be obtained). Therefore, according to the present invention, it is possible to suppress the light measurement unit from detecting light, which is blocked by impurities.

In addition, any sample corresponding to the intended usage can be used in the inspection apparatus using the chip according to the present invention. For example, in a medicine use, body fluid, such as blood and urine, can be used as a sample. Moreover, for example, in an environmental use, water of a river can be used as a sample. Furthermore, for example, in a food use, a solvent in which a mold adhering to food is dissolved can be used as a sample. Since the inspection apparatus using a chip according to the present invention can apply a centrifugal force to the chip effectively, for example, when blood liquid, such as blood, consists of two or more liquids, that is, liquid containing blood plasma and liquid containing a blood cell, each liquid can be separated by applying a centrifugal force, so that one ingredient can be examined. The body liquid obtained from a human body is separated, for example, in several minutes to tens of minutes by applying a large centrifugal force such as 500 G, and a large centrifugal force such as 500 G is also added to the chip that stores the sample. Since the inspection apparatus using a chip according to the present invention suppresses flying out of the chip due to the centrifugal force, as mentioned above, the present invention can be especially suitably applied to usage in which such a large centrifugal force is applied to a sample, which is body liquid, such as blood and urine.

The preceding description has been presented only to illustrate and describe exemplary embodiments of the present inspection apparatus using a chip. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

What is claimed is:

1. A control method of an inspection apparatus using a chip, comprising the steps of:
    providing the inspection apparatus, comprising:
        a rotor that holds a chip;
        a measurement room in which the rotor is provided and a through hole is formed;
        a light source that emits light for measurement to the chip through the through hole;
        a light measurement unit that detects the light from the chip;
        a rotation drive mechanism that rotates the rotor;
        a cover member that selectively covers and uncovers an opening portion provided between the through hole and an opening of the light measurement unit through which light passes;
        a hole portion formed in the rotor;
        a projection portion that can be inserted in the hole portion; and
        a drive mechanism that moves the projection portion and the cover member,
        such that while the projection portion is inserted in or removed from the hole portion according to a rotational position of the drive mechanism the cover member is moved to cover or uncover the opening portion;
    inserting the projection portion in the hole portion where the opening portion is closed;
    removing the projection portion from the hole portion when covering the opening portion and rotating the rotor; and
    emitting light and performing detection by the light measurement unit when not covering the opening portion.

2. The control method of the inspection apparatus using a chip according to claim 1, wherein the inspection apparatus further comprises:
    a movable body movable by the drive mechanism;
    a dog member in the movable body; and
    a position sensor that detects a movement position of the dog member,
    wherein a rotational position of the drive mechanism is controlled based on a detection result of the position sensor.

3. The control method of the inspection apparatus using a chip according to claim 2, further comprising the steps of:
    inserting the projection portion in the hole portion where the opening portion is closed;
    removing the projection portion from the hole portion when covering the opening portion and rotating the rotor; and
    emitting light and performing detection by the light measurement unit when not covering the opening portion.

4. The control method of the inspection apparatus using a chip according to claim 1, wherein the opening portion of the inspection apparatus is covered by the cover member when the chip is not irradiated with the light and when detection is not carried out by the light measurement unit.

* * * * *